United States Patent
Khosla et al.

(10) Patent No.: US 9,333,019 B2
(45) Date of Patent: May 10, 2016

(54) WIRE DRIVER

(71) Applicant: Arthrex, Inc., Naples, FL (US)

(72) Inventors: Rudraksh Khosla, Naples, FL (US); G. Scott Sherman, Naples, FL (US); Thomas Jindra, Ostermiething (AT)

(73) Assignee: Arthrex, Inc., Naples, FL (US)

( * ) Notice: Subject to any disclaimer, the term of this patent is extended or adjusted under 35 U.S.C. 154(b) by 130 days.

(21) Appl. No.: 13/841,780

(22) Filed: Mar. 15, 2013

(65) Prior Publication Data

US 2014/0276890 A1 Sep. 18, 2014

(51) Int. Cl.
*A61B 17/58* (2006.01)
*A61B 17/88* (2006.01)
*A61B 17/16* (2006.01)

(52) U.S. Cl.
CPC ............ *A61B 17/8861* (2013.01); *A61B 17/162* (2013.01); *A61B 17/1697* (2013.01)

(58) Field of Classification Search
CPC ........... A61B 17/8869; A61B 17/8861; A61B 17/842; A61B 17/8897; A61B 17/1697; A61B 17/162
USPC ................................ 606/103, 104, 80, 82, 79
See application file for complete search history.

(56) References Cited

U.S. PATENT DOCUMENTS

| | | | |
|---|---|---|---|
| 4,091,880 A | | 5/1978 | Troutner et al. |
| 4,441,563 A | * | 4/1984 | Walton, II ............... 173/213 |
| 5,431,659 A | * | 7/1995 | Ross et al. ............... 606/103 |
| 5,478,093 A | | 12/1995 | Eibl et al. |
| 5,788,697 A | * | 8/1998 | Kilpela et al. ............ 606/74 |
| 5,794,715 A | * | 8/1998 | Norman ................... 173/104 |
| 5,902,306 A | * | 5/1999 | Norman ................... 606/104 |
| 2008/0224427 A1 | | 9/2008 | Schwarz et al. |
| 2013/0245629 A1 | * | 9/2013 | Xie ................. A61B 17/162 606/80 |

FOREIGN PATENT DOCUMENTS

| | | |
|---|---|---|
| AT | 400 665 B | 2/1996 |
| DE | 1 99 45 322 A1 | 5/2001 |
| DE | 10 2007 012 859 A1 | 9/2007 |
| EP | 2 238 920 A1 | 10/2010 |

* cited by examiner

*Primary Examiner* — Eduardo C. Robert
*Assistant Examiner* — Tessa Matthews
(74) *Attorney, Agent, or Firm* — Blank Rome LLP

(57) ABSTRACT

A driver for medical wires has a hollow drive shaft, rotatable about a rotation axis. The hollow drive shaft has a distal end and a proximal end. Furthermore, a plurality of clamping jaws penetrates under an angle into the hollow drive shaft close to its distal end. The clamping jaws are moved into or out of the hollow drive shaft by means of a jaw guide mounted slidable parallel to the rotation axis and movably connected to the clamping jaws. An actuator is provided to shift the jaw guide parallel to the rotation axis and therefore modify the penetration depth of the clamping jaws.

9 Claims, 3 Drawing Sheets

WIRE DRIVER

BACKGROUND

The invention relates to a surgical wire driver adapted to insert a circular prosthetic device into or through bones to provide support and fixation to bone structures and fractured bones, and particularly to a rotary wire-inserting device utilizing a surgical wire.

In the prior art, prosthetic wire drivers are known, driving the wire and letting the wire bore its own hole into the bone. Such an instrument is disclosed in U.S. Pat. No. 4,091,880. It has a split spring collet, holding a specifically adapted wire of a substantially circular cross-section, having one or more flats to provide anti-rotational keying with the collet. The disadvantage of the prior art is the requirement for special wires and the complex adjustment and setting of the collet, which requires an Allen wrench.

A surgical chuck which allows comparatively quick fastening and releasing is disclosed in DE 199 45 322 B4. Here, clamping jaws, which are preloaded by a spring, are used. The drawback is the complex configuration, missing a control on locking/release actions. Furthermore, a significant access length of the wire is required to penetrate into the chuck and interact with the clamping jaws.

A surgical hand piece is disclosed in EP 2 238 920 A1, which is included herein by reference.

SUMMARY

The embodiments of the present invention are directed to improve surgical wire drivers by providing a simplified mechanical design, which can handle wires having a minimal excess length for holding the wire, and which can be operated easily.

In an embodiment, the wire driver has an at least partially hollow drive shaft, which may be driven by a motor or coupled to a hand piece by a shaft connector and may rotate around a rotation axis. It has a proximal and a distal end. The distal end of the drive shaft is hollow and has a diameter sufficiently large to hold a surgical wire. The proximal end of the drive shaft preferably is open to allow penetration of long surgical wires, but it may also be closed. Close to the distal end of the drive shaft, there is a plurality of clamping jaws. Preferably, there are three clamping jaws, which can be moved to penetrate into the inner volume of the hollow drive shaft. It is preferred, if all clamping jaws are moved with the same distance at the same time. The clamping jaws define an opening sufficiently large to guide and hold the wire. Preferably, the jaws are preloaded by a spring, pressing the jaws towards the distal end, resulting in pressing the jaws together or to the wire and therefore holding the wire. The clamping jaws are operated by a jaw guide which is mounted slidable parallel to the rotation axis. The jaw guide is movably connected to the clamping jaws to move the clamping jaws in or out of the hollow drive shaft. For moving the jaw guide, an actuator may be provided. This actuator preferably generates a linear motion of the jaw guide parallel to the rotation axis. It is further preferred, if the actuator is a lever, which preferably is tiltable about a lever axis.

According to a further aspect, an actuator spring is provided to preload the actuator and therefore to preload the clamping jaws via the jaw guide. Furthermore, a slider may be operated by the actuator. The slider may be mounted slidable parallel to the rotation axis, holding a drive shaft bearing which is in contact with the jaw guide. It is further preferred, if a jaw guide spring is provided to hold the jaw guide against the drive shaft bearing.

It is further preferred, if the clamping jaws have at least one pin contact surface which contacts the surgical wire preferably causes friction to the wire. For moving the clamping jaws, it is preferred, if the clamping jaws have a guiding cutout, which may interact with at least one cam provided at the jaw guide.

To improve connection to a medical handpiece, it is preferred, if a flange is provided at the proximal end of the driver. Furthermore an input shaft may be provided, which is rotatably coupled with the drive shaft, to be driven by a medical handpiece.

Examples of medical wires or pins are Kirschner wires or K-wires, which may be sharpened, smooth stainless steel pins.

It is further preferred, if there is a housing having openings and/or gaps to provide for a quick gas and/or liquid exchange to simplify sterilization.

Another embodiment is a method for driving of a medical wire includes the steps of:
  inserting the medical wire into a hollow drive shaft (22), rotatable about a rotation axis (13), the hollow drive shaft has a distal end and a proximal end,
  clamping the medical wire by a plurality of clamping jaws (30, 31, 32) which are moved to penetrate under an angle into the hollow drive shaft close to its distal end,
  moving the clamping jaws (30, 31, 32) into or out of the hollow drive shaft by a jaw guide (33) mounted slidable parallel to the rotation ax-is (13) and movably connected to the clamping jaws to increase friction between the medical wire and the clamping jaws.

The method may be combined with any other embodiment disclosed herein.

Another embodiment relates to a method for fixing of bones or parts thereof by driving a medical wire or pin by using a driver for medical wires as disclosed herein or by using a method for driving of a medical wire as disclosed herein.

A further embodiment relates to a medical handpiece having a driver for medical wires according to any one of the previous claims.

As the clamping jaws are arranged close to the distal end of the drive shaft and therefore close to the distal end of the pin driver, there is only a minimal excess length of the medical wire necessary for holding the wire. Due to the simple operation by shifting or moving the actuator or lever, a medical wire may quickly be held or released. There may also be a quick sequence of holding and releasing operations by simply pushing and pulling the actuator or lever. The driver must not be adapted to specific wire diameters. Instead, a simple locking action is sufficient. When looking or clamping the wire, the clamping jaws penetrate into the hollow channel of the drive shaft until the pin contact surfaces of the clamping jaws contact the wire and lock it. Then no further movement of the clamping jaws is possible.

Due to the simple design with a low number of simple mechanical components together with gaps and openings for liquid and/or gas exchange, the driver for medical wires can be easily sterilized.

BRIEF DESCRIPTION OF THE DRAWINGS

In the following, embodiments of the invention are described in reference to examples, drawings, and without limitation of the general inventive concept.

Figure 1:
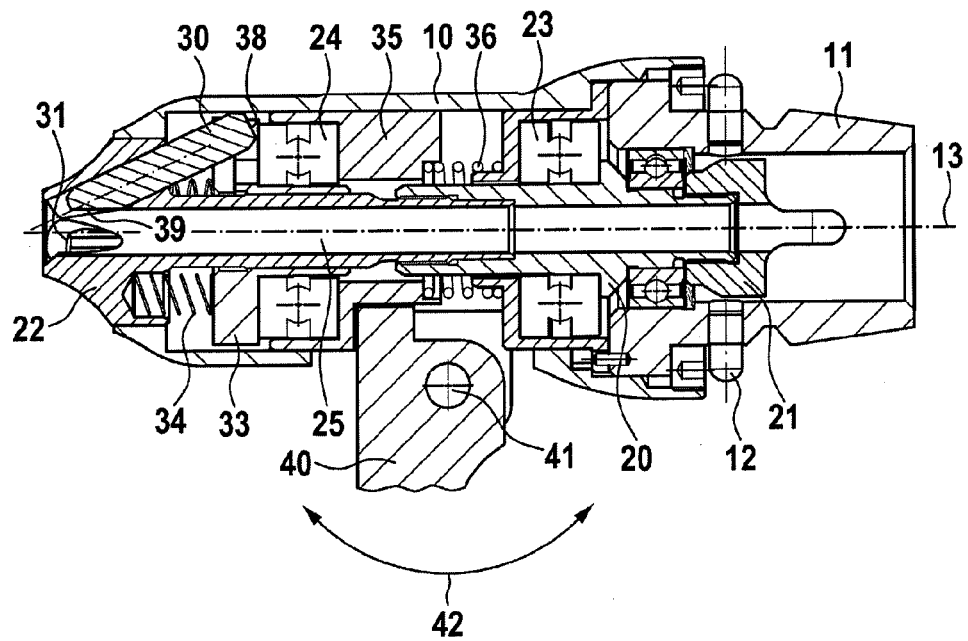
FIG. 1 shows a pin driver according to an embodiment in an open state.

While the invention is susceptible to various modifications and alternative forms, specific embodiments thereof are shown by way of example in the drawings and will herein be described in detail. It should be understood, however, that the drawings and detailed description thereto are not intended to limit the invention to the particular form disclosed, but on the contrary, the intention is to cover all modifications, equivalents and alternatives falling within the spirit and scope of the present invention as defined by the appended claims.

DETAILED DESCRIPTION

In FIG. 1, a preferred embodiment of a pin driver is shown. This pin driver is an attachment, which for example may be attached to a hand piece as disclosed in EP 2 238 920 A1. It is understood that the pin driver may also be part of a hand piece, and may therefore be integrated or enclosed into such a hand piece. The pin driver has a housing 10, having a distal side (shown at the left side of the figure) and a proximal side (shown at the right side of the figure). This housing contains the mechanical components. This specific embodiment of a pin driver has a flange 11 for attachment to a hand piece. The flange 11 may have a conical shape and it may have at least one attachment ball 12. There is an input shaft 20 which is rotatable around a rotation axis 13, and which is driven by a hand piece or a motor. The input shaft 20 may be connected to a hand piece by shaft connector 21 for transmitting torque. For holding a wire, a drive shaft 22 is provided. This drive shaft 22 may be at least rotatably fixed to the input shaft, or it may be a part thereof. The drive shaft 22 has a hollow channel 25 for accommodating a wire. The drive shaft 22 has an open end at the distal side and may be either open or closed towards the proximal side. There may be a drive shaft bearing 24 for supporting the drive shaft 22. Furthermore, there may be an input shaft bearing 23 for supporting the input shaft 20. For holding a wire, clamping jaws 30, 31, 32 are provided. Preferably, there are three clamping jaws having an angular displacement of 120° to each neighbored jaw. Alternate embodiments may include a different number of clamping jaws, like a single jaw, two jaws, or a higher number of jaws. The clamping jaws are at an angle of less then 90°, preferably less than 40°, most preferably between 20° and 30° with respect to the rotation axis. A jaw guide 33 is provided for pulling the jaws back into proximal direction or pushing the jaws forward into distal direction, therefore enlarging or decreasing the opening between the jaws. The jaw guide preferably has a ring-shaped structure, and at least one cam to interact with a jaw. The jaw guide is moved into proximal or distal direction parallel to the rotating axis. Preferably, it rotates together with the jaws, which are rotatably fixed in channels of the drive shaft. For actuating the rotating jaw guide 33, preferably a non-rotating slider 35 is provided. This slider is coupled to the jaw guide 33 by means of the drive shaft bearing 24. For preloading this bearing and holding the jaw guide 33 to this bearing, a jaw guide spring 34 may be provided. The slider 35, which is non-rotatable, but slidable into proximal and distal direction, preferably is operated by a Ilever 40, which preferably is tilted around a lever axis 41 into two directions 42. There may be an actuator spring 36 to preload the slider 35 and/or the lever 40.

Figure 2:
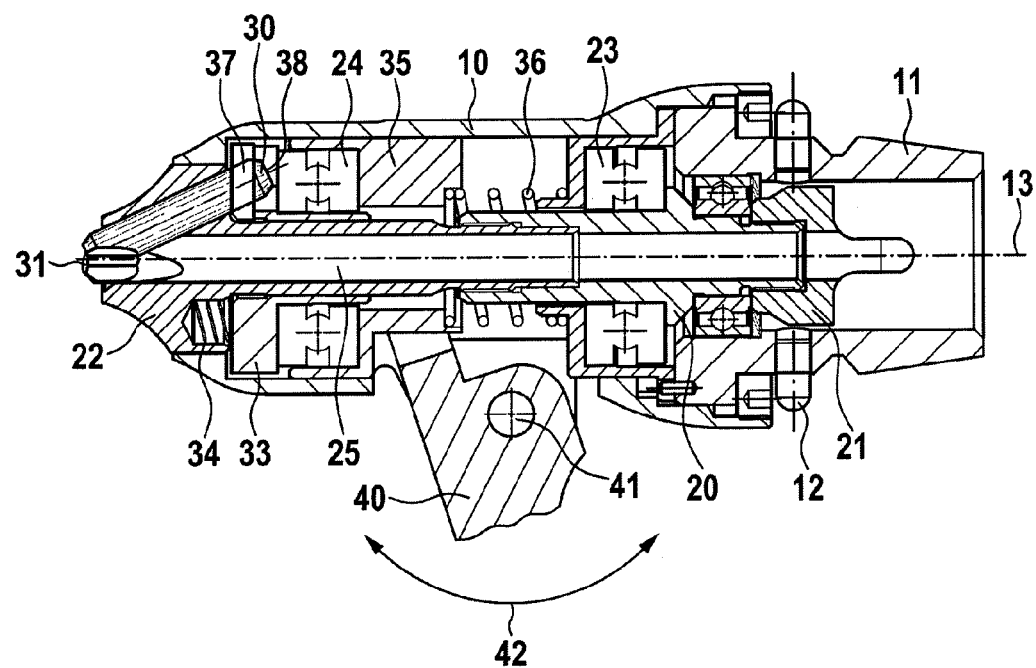
FIG. 2 shows a pin driver in a closed state.

The operation of the pin driver is as follows: in an idle state, the lever 40 is released, as shown in FIG. 2. It is held in this state by the actuator spring 36, which furthermore presses slider 35, drive shaft bearing 24, and jaw guide 33 into distal direction, causing the jaws also to move into distal direction and to close the opening. When a wire is inserted into the pin driver from the distal side, it will first be pushed against the clamping jaws' distal side. Due to the low angle of the clamping jaws with respect to the rotating axis, the clamping jaws can be pushed backwards into proximal direction against the force of the actuator spring 36. By this movement, the clamping jaws increase their opening until the wire may slide through the opening into the hollow channel 25 of drive shaft 22. Now, the pin contact surfaces 39 of the clamping jaws 30, 31, 32 are in close contact with the surface of the wire and press on the wire, therefore allowing to transfer torque from the drive shaft, and therefore to rotate the pin. For releasing the pin, the lever 40 may be pushed into a distal direction, therefore releasing force asserted by actuator spring 36 to the clamping jaws and moving the clamping jaws into proximal direction, causing the opening between the clamping jaws to increase and release the wire. It is preferred to manually open the opening before inserting a wire by actuating the lever. Opening the jaws is also necessary, if a wire will be inserted from the proximal side of the pin driver.

Generally, the lever is held in proximal direction by the actuator spring 36, closing the clamping jaws. The lever may be moved into distal direction for opening the clamping jaws. It may further be held in proximal direction to increase the clamping force of the clamping jaws.

In FIG. 2, a pin driver in a closed state of the clamping jaws is shown. Here, the lever 40 is pressed in proximal direction by the actuator spring 36, while it has manually been held in distal direction by the operator, as shown in FIG. 1. Compared to FIG. 1, here, the slider 35 together with the drive shaft bearing 24 and the jaw guide 33 are displaced in distal direction, pushing the clamping jaws in distal direction, and therefore closing the opening between the clamping jaws. A further detail of the clamping jaws is shown in this figure. To push the clamping jaws into distal direction and to pull them into proximal direction, a guiding cutout 37 is provided. This cutout interfaces with at least one cam for each clamping jaw. The cams are part of the jaw guide 33.

Figure 3:
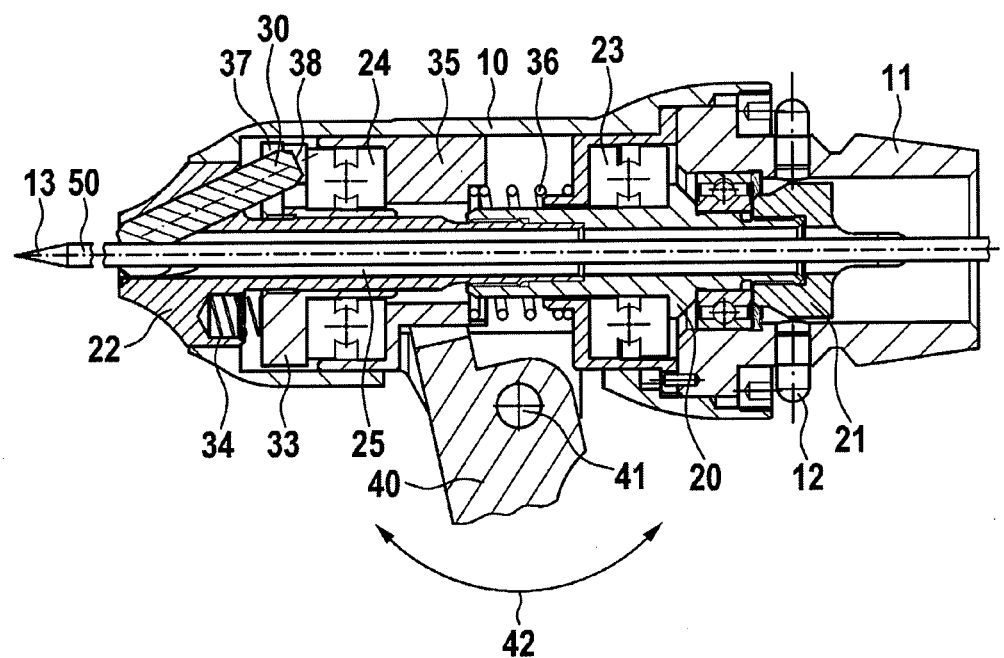
FIG. 3 shows a wire driver with inserted wire.

In FIG. 3, a pin driver with an inserted wire 50 is shown. The wire is centered at the rotation axis 13. For holding the wire, the clamping jaws and the other movable parts are in an intermediate position adapted to the diameter of the wire.

Figure 4:
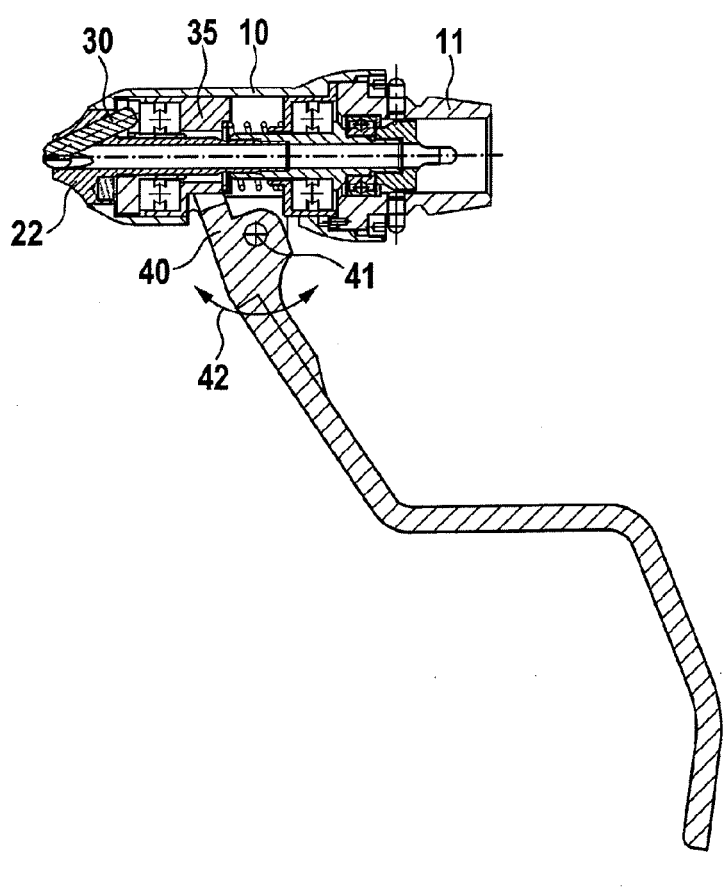
FIG. 4 shows a sectional side view of the whole pin driver including the lever.

In FIG. 4, a sectional side view of the pin driver including the lever 40 is shown.

Figure 5:
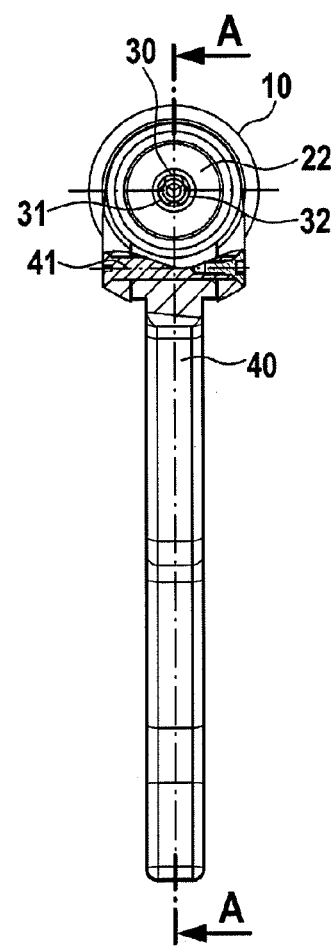
FIG. 5 shows a sectional front view of the whole pin driver including the lever.

In FIG. 5, a sectional front view of the pin driver including the lever 40 is shown.

It will be appreciated to those skilled in the art having the benefit of this disclosure that this invention is believed to provide a driver for medical wires. Further modifications and alternative embodiments of various aspects of the invention will be apparent to those skilled in the art in view of this description. Accordingly, this description is to be construed as illustrative only and is for the purpose of teaching those skilled in the art the general manner of carrying out the invention. It is to be understood that the forms of the invention shown and described herein are to be taken as the presently preferred embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

LIST OF REFERENCE NUMERALS 10 housing
11 flange
12 attachment bolt
13 rotation axis
20 input shaft
21 shaft connector
22 drive shaft
23 input shaft bearing
24 drive shaft bearing
25 hollow channel
30, 31, 32 clamping jaws
33 jaw guide
34 jaw guide spring
35 slider
36 actuator spring
37 guiding cutout
38 jaw proximal end
39 pin contact surface
40 lever
41 lever axis
42 lever tilt
50 wire

The invention claimed is:

1. A driver for medical wires including:
   a hollow drive shaft, rotatable about a rotation axis, the hollow drive shaft having an open distal end and a proximal end;
   a plurality of clamping jaws each having a longitudinal axis and each being movable along its longitudinal axis to penetrate under an angle into the hollow drive shaft close to its distal end, the plurality of clamping jaws defining an opening for guiding and holding a medical wire;
   a jaw guide mounted slidable parallel to the rotation axis and movably connected to the clamping jaws to move the clamping jaws into or out of the hollow drive shaft, the jaw guide pulling the clamping jaws back into a proximal direction or pushing the clamping jaws forward into a distal direction, therefore enlarging or decreasing the opening between the clamping jaws; and
   an actuator to shift the jaw guide parallel to the rotation axis and therefore modify the penetration depth of the clamping jaws,
   wherein the clamping jaws are located outside of the hollow drive shaft when the jaw guide pulls the clamping jaws out of the hollow drive shaft back into the proximal direction, and wherein the clamping jaws are located within the hollow drive shaft when the jaw guide pushes the clamping saws forward into the distal direction to clamp and hold the medical wire; and wherein the clamping jaws have a guiding cutout which interacts with a cam of the jaw guide.

2. The driver for medical wires according to claim 1, wherein the actuator is a lever tiltable about a lever axis.

3. The driver for medical wires according to claim 1, wherein an actuator spring is provided for preloading the actuator and therefore the clamping jaws.

4. The driver for medical wires according to claim 1, wherein a slider operated by the actuator is mounted slidable parallel to the rotation axis holding a drive shaft bearing, the drive shaft bearing being in contact with the jaw guide.

5. The driver for medical wires according to claim 4, wherein a jaw guide spring is provided to hold the jaw guide against the drive shaft bearing.

6. The driver for medical wires according to claim 1, wherein the clamping jaws have at least one pin contact surface.

7. The driver for medical wires according to claim 1, wherein an input shaft is rotatably coupled with the drive shaft to be driven by a medical handpiece.

8. The driver for medical wires according to claim 1, wherein a flange is provided to connect the driver to a medical handpiece.

9. A medical handpiece having a driver for medical wires including:
   a hollow drive shaft, rotatable about a rotation axis, the hollow drive shaft has an open distal end and a proximal end;
   a plurality of clamping jaws each having a longitudinal axis and each being movable along its longitudinal axis to penetrate under an angle into the hollow drive shaft close to its distal end, the plurality of clamping jaws defining an opening for guiding and holding a medical wire;
   a jaw guide mounted slidable parallel to the rotation axis and movably connected to the clamping jaws to move the clamping jaws into or out of the hollow drive shaft, the jaw guide pulling the clamping jaws back into a proximal direction or pushing the clamping jaws forward into a distal direction, therefore enlarging or decreasing the opening between the clamping jaws; and
   an actuator to shift the jaw guide parallel to the rotation axis and therefore modify the penetration depth of the clamping jaws,
   wherein the clamping jaws are located outside of the hollow drive shaft when the jaw guide pulls the clamping jaws out of the hollow drive shaft back into the proximal direction, and wherein the clamping jaws are located within the hollow drive shaft when the jaw guide pushes the clamping jaws forward into the distal direction to clamp and hold the medical wire; and wherein the clamping jaws have a guiding cutout which interacts with a cam of the jaw guide.

* * * * *